US00PP20816P2

(12) United States Plant Patent
Growns

(10) Patent No.: US PP20,816 P2
(45) Date of Patent: Mar. 9, 2010

(54) WAXFLOWER PLANT NAMED 'MATILDA'

(50) Latin Name: ***Chamelaucium* hybrid *(Chamelaucium uncinatum×Chamelaucium megalopetalum)***
Varietal Denomination: Matilda

(75) Inventor: Digby James Growns, Willetton (AU)

(73) Assignee: Western Australian Agriculture Authority, South Perth (AU)

( * ) Notice: Subject to any disclaimer, the term of this patent is extended or adjusted under 35 U.S.C. 154(b) by 0 days.

(21) Appl. No.: 12/229,138

(22) Filed: Aug. 20, 2008

(51) Int. Cl.
*A01H 5/00* (2006.01)

(52) U.S. Cl. ..... Plt./226

(58) Field of Classification Search ..... Plt./226
See application file for complete search history.

*Primary Examiner*—Annette H Para
(74) *Attorney, Agent, or Firm*—Michelle Bos

(57) ABSTRACT

'Matilda' is a new and distinct waxflower plant (interspecific *Chamelaucium* hybrid) notable for its early flowering, compact growth habit, and dense terminal cover of large white flowers that age to white with a diffuse magenta to maroon ring.

5 Drawing Sheets

Latin name of the genus and species of the plant claimed: Interspecific *Chamelaucium* hybrid (*Chamelaucium uncinatum×Chamelaucium megalopetalum*).

Variety denomination: 'Matilda'.

BACKGROUND OF THE INVENTION

'Matilda' is a new waxflower plant that originated as a seedling produced in a sexual breeding program conducted by the State of Western Australia at its Medina Research Station and at its South Perth nursery and laboratories. Originally identified by its breeder's reference 'WX47', 'Matilda' was selected from seedlings of a controlled cross performed in 1999 between female parent '5001/720-8', an intraspecific hybrid within *C. uncinatum* (not patented), and male parent *C. megalopetalum* 'CM 6.6' (not patented). 'Matilda' was first asexually propagated at South Perth in 2002 from cuttings, and has been shown to remain true to type over successive generations.

'Matilda' is distinguishable from its female parent '5001/720-8' by a number of features, as described in Table 1 below:

TABLE 1

| Characteristic | 'Matilda' | '5001/720-8' |
|---|---|---|
| Leaf size | Medium | Long |
| Leaf shape | Narrow ovate with acute apex | Lanceolate with hooked apex |
| Leaf cross section | Triangular with indented upper surface | Terete |
| Flower color | White aging to white with distinct deep magenta to maroon ring | Almost white aging to pink |
| Flower size | Large | Small |

'Matilda' is distinguishable from its male parent 'CM 6.6' by a number of features, as described in Table 2 below:

TABLE 2

| Characteristic | 'Matilda' | 'CM 6.6' |
|---|---|---|
| Growth habit | Compact | Medium upright |
| Leaf shape | Narrow ovate with acute apex | Obovate with obtuse apex |
| Flower shape | Open | Cupped |
| Flower color | White aging to white with distinct deep magenta to maroon ring | White aging to magenta and maroon spots and uneven patches |
| Flower size | Large | Small |

'Matilda' is also distinguishable from other known waxflower varieties. A comparison of 'Matilda' to 'Bridal Pearl' (unpatented), the most similar variety of common knowledge, is set forth in Table 3 below:

TABLE 3

| Characteristic | 'Matilda' | 'Bridal Pearl' |
|---|---|---|
| Growth habit | Compact | Medium upright |
| Leaf shape | Narrow ovate with acute apex | Obovate with obtuse apex |
| Flower shape | Open | Cupped |
| Flower color | White aging to white with distinct deep magenta to maroon ring | White aging to magenta and maroon spots and uneven patches |
| Flower size | Large | Medium |

BRIEF DESCRIPTION OF THE PHOTOGRAPHS

DETAILED BOTANICAL DESCRIPTION

Figure 1:
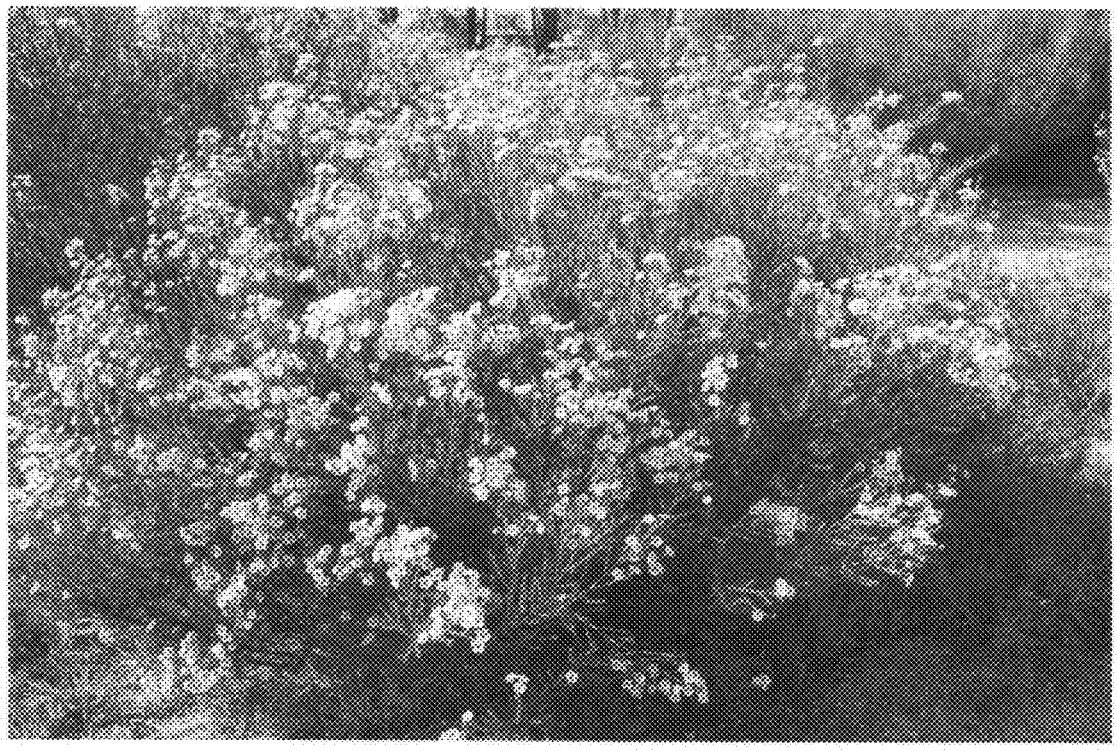
FIG. 1 is a photograph of 'Matilda' growing outdoors.
Figure 2:
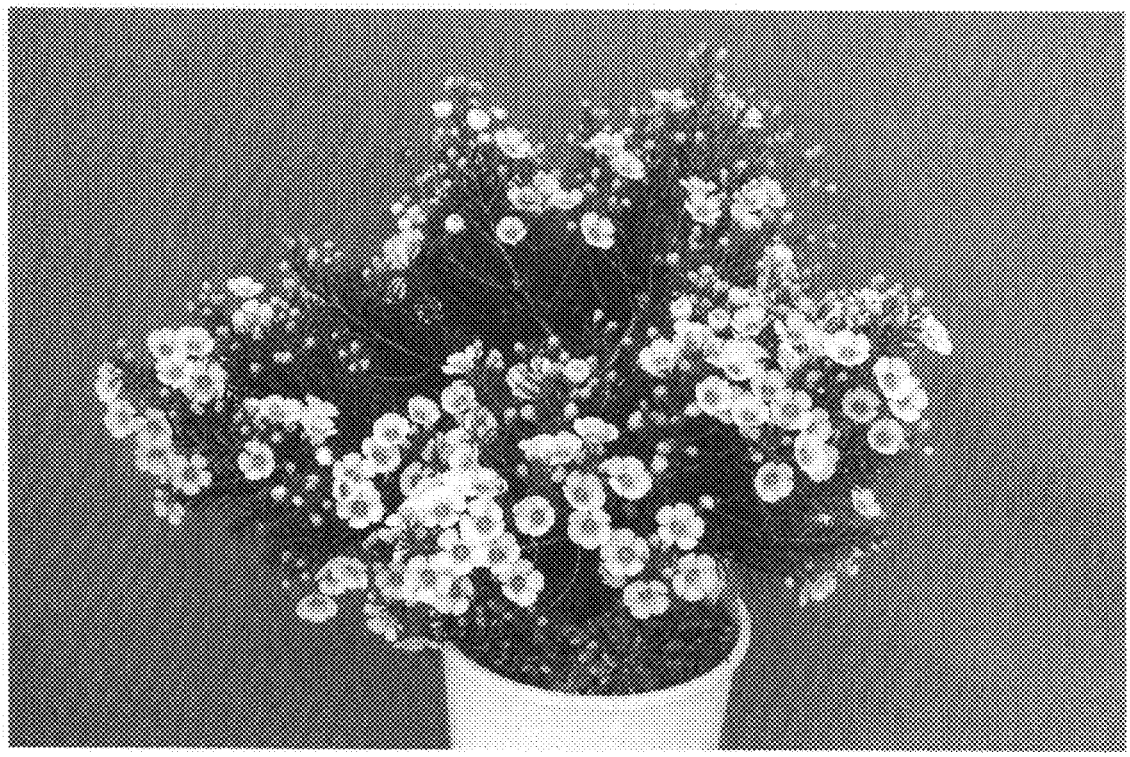
FIG. 2 is a photograph of a potted plant of 'Matilda'.
Figure 3:
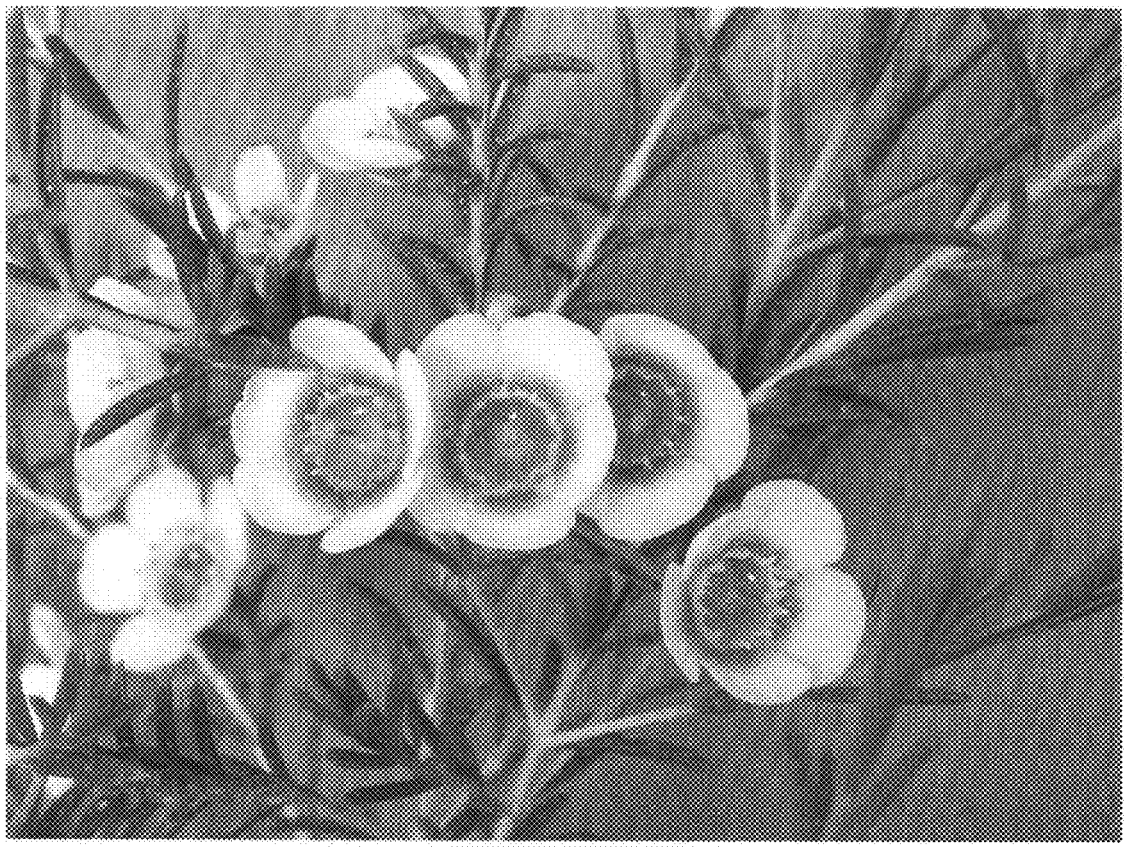
FIG. 3 is a photograph of the flowers of 'Matilda'.
Figure 4:
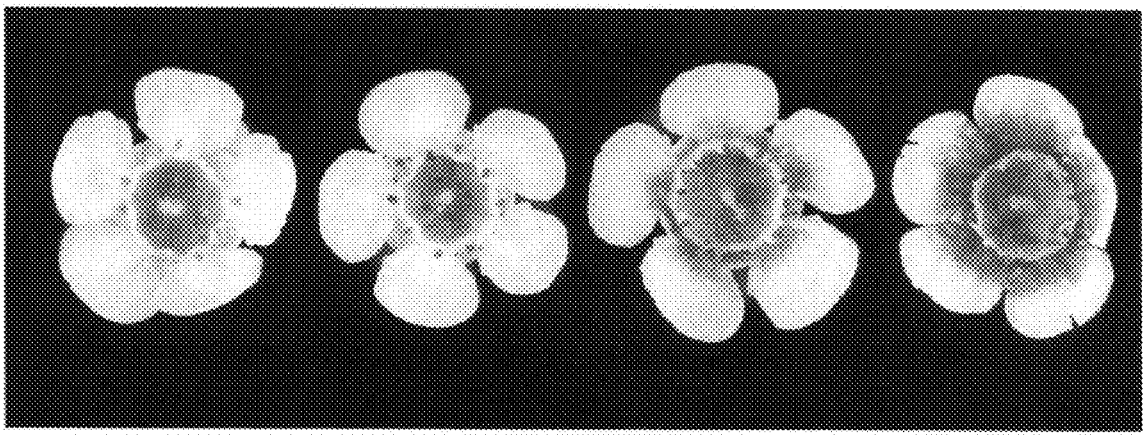
FIG. 4 is a photograph of the flowers of 'Matilda', showing the typical progression of coloration as the flowers age.
Figure 5:
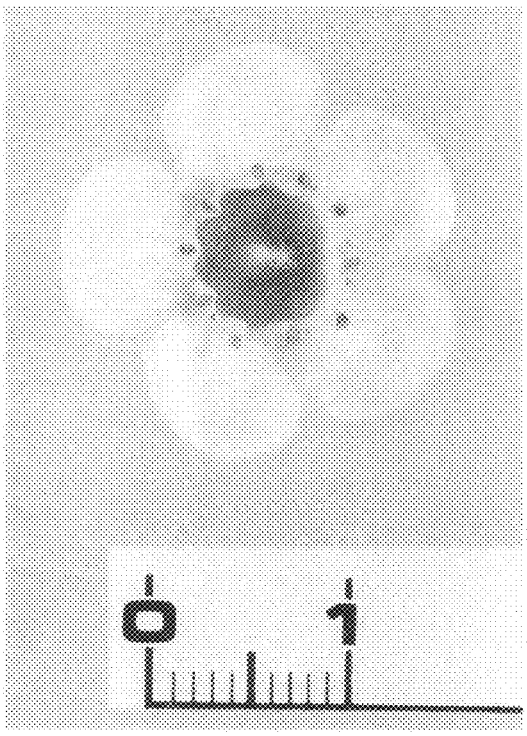
FIGS. 5 and 6 are close-up photographs of a young flower of 'Matilda'.
Figure 6:
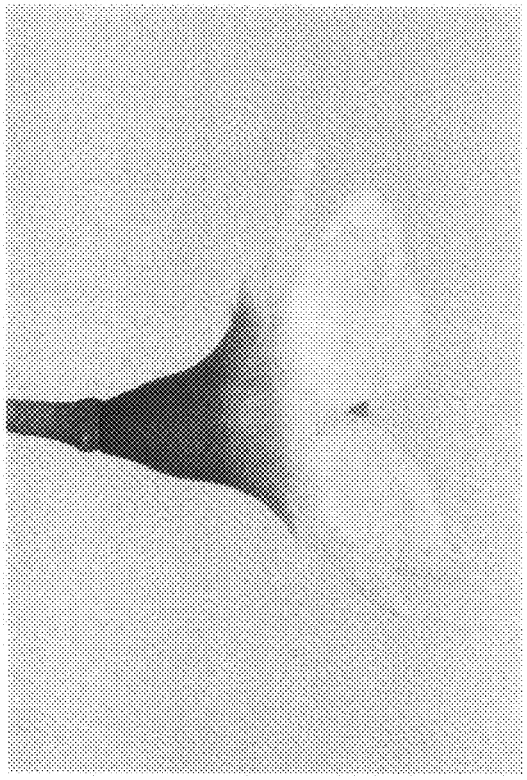
Figure 7:
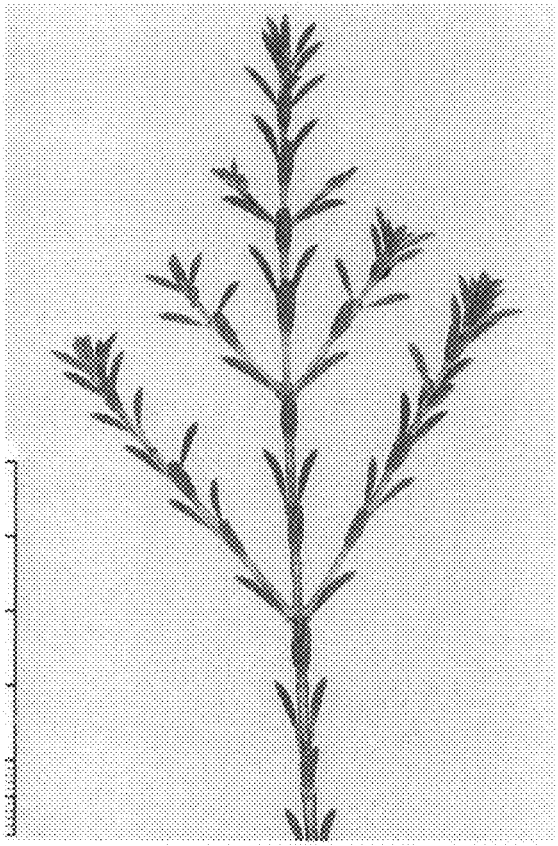
FIG. 7 is a photograph of a branch and leaves of 'Matilda'.
Figure 8:
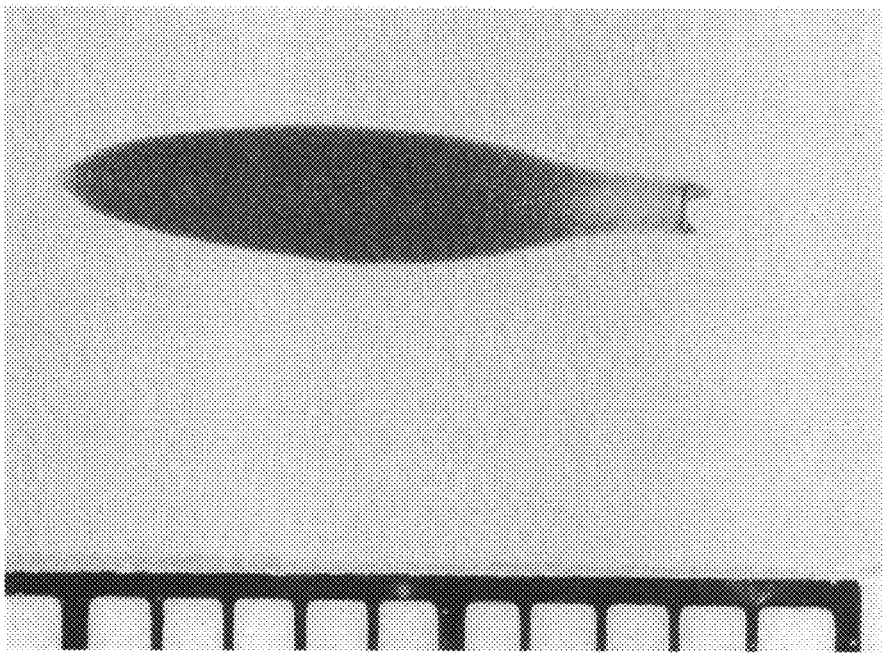
FIG. 8 is a close-up photograph of a leaf of 'Matilda'.
Figure 9:
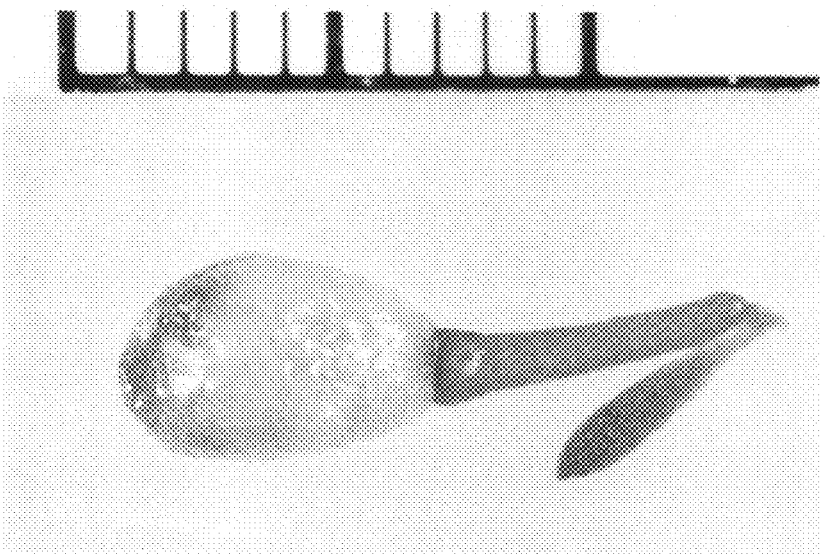
FIG. 9 is a close-up photograph of a flower bud of 'Matilda'.
Figure 10:
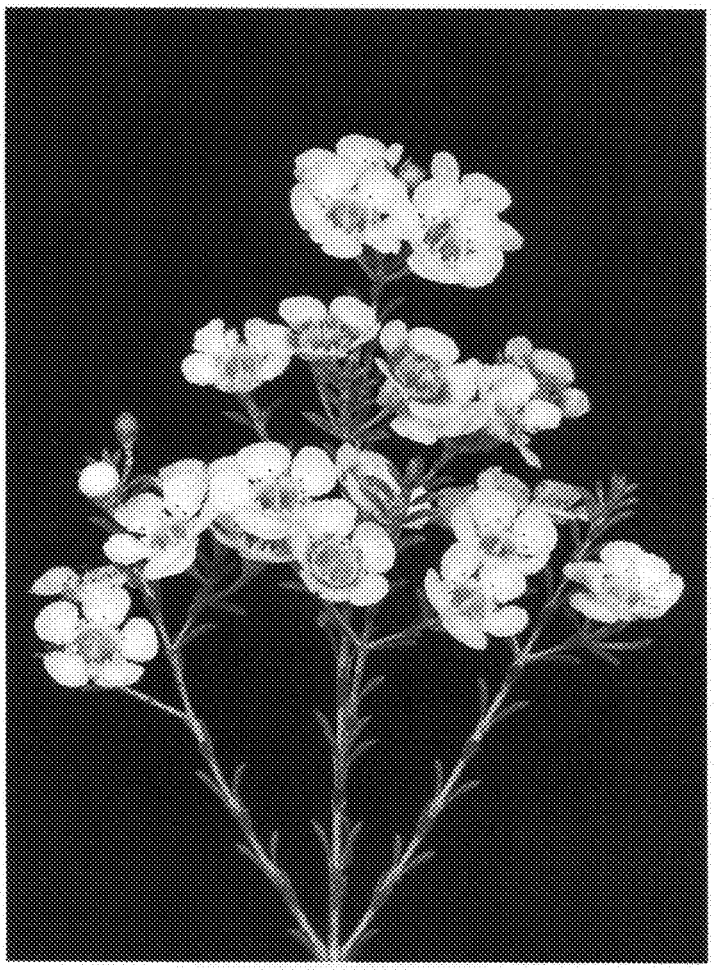
FIG. 10 is a photograph of a branch, leaves and flowers of 'Matilda.'

The following detailed botanical description is based on observations of four year old plants of the waxflower variety named 'Matilda' growing at Medina Research Station, Medina, Western Australia. All colors are described according to The Royal Horticultural Society Colour Chart (2001). It should be understood that the characteristics described will vary somewhat depending upon cultural practices and climatic conditions, and can vary with location and season. Quantified measurements are expressed as an average of measurements taken from a number of individual plants of the new variety. The measurements of any individual plant, or any group of plants, of the new variety may vary from the stated average.

Plant:

*Summary.*—'Matilda' is an early flowering compact medium height bush with dense terminal cover of large (19 mm) white wax flowers that age to a magenta to maroon diffuse ring.

*Growth habit.*—Branching upright shrub growing to a height of 1 m and bush diameter of 1.3 m.

*Flowering stem length.*—50 cm.

Leaves:

*Leaf arrangement.*—Opposite.

*Leaf density.*—Main branch: about 10 pairs per 6 cm branch length. Secondary branch: 16 pairs of leaves branch 5 cm in length.

*Arrangement.*—Held at about 25 to 30 degree angle to stem.

*Aroma.*—Eucalyptus or citrus aroma when leaves are crushed.

*Leaf inter node length.*—Average 14.0 mm on main branch, and 9.3 mm on secondary branch.

*Leaf size.*—Length 8.7 mm, width 1.7 mm.

*Leaf shape.*—Narrowly obovate with acute apex.

*Leaf surface texture.*—Glabrous glandular, leathery, shiny.

*Leaf margin.*—Entire.

*Leaf base.*—Sessile truncate to stem.

*Leaf cross section.*—Triangular with indented upper surface.

*Leaf color.*—New growth, upper and lower surface yellow-green 144B to 144C; mature leaves, upper and lower surface green 137B.

*Leaf division.*—Simple.

*Leaf venation.*—None visible.

Flower:

*Flower bud.*—Fresh buds — cone shaped with smooth shiny surface color yellow-green 145B and tip of bud color orange-red N30; diameter 3.6 mm, length 5.2 mm. Older buds — more elongated with papery operculum, coarse, surface color grey-brown N199B to N199C; diameter 4.7 mm, length 7.4 mm.

*Flowering season.*—Early July to Late August (Medina Research Station, Medina, Western Australia).

*Flower longevity.*—60 days.

*Flower quality.*—High.

*Flowering time.*—Early.

*Flower description.*—Flowers slightly cupped and petals slightly overlapping to touching, round in shape, upper and lower surface are glabrous waxy, entire margin, truncate base and fused to calyx, rounded apex. Flower color undergoes changes as it matures (lower and upper surface same coloration).

*Petal color.*—On day of opening white 155D; When partially developed, outer petal white 155D, base of petal starting to form patches of red-purple 58B; When fully developed, outer petal white 155D, base of petal red-purple 61A, forming a diffused ring on the flower.

*Flower arrangement.*—Corymb.

*Flower type.*—Single flower.

*Flowering habit.*—Terminal, panicle florescence.

*Flower shape.*—Cup-shaped.

*Flower diameter.*—Average 18.6 mm; depth 11.3 mm (top of stigma to bottom of ovary).

*Flowering branch angle.*—Overlapping.

*Flowering attitude of petals on day of opening.*—Semi erect.

*Flowering branch angle 2 weeks after opening.*—Nearly horizontal.

*Flower.*—Length of sepal in relation to length of petal — less than one-third.

*Petiole (pedicle) length.*—Long 12.9 mm, aspect 25° to 35°.

*Hypanthium shape.*—Cylindrical with longitudinal furrowing on half length.

*Hypanthium diameter.*—Small, 7.1 mm.

*Hypanthium main color at middle part on day of opening of flower.*—Yellow green 145C; 4 weeks after opening of flower yellow green 145B.

*Nectaries.*—About 6 mm in diameter, color see hypanthium.

*Flower petals.*—Usually 5, occasionally 6–7, round shape; fused sepals at base to hypanthium, with rounded outer separate lobes arranged alternately between petals; tube portion fluted; fused sepals yellow-green 145B to 146B; lobed sepals; new petals white 155D, developing an inner arc red-purple 58A to 61A with outer arc white 155D as the petals age.

*Petal shape.*—Slightly cupped and undulation of margins weak.

*Petal texture.*—Waxy, glabrous.

*Petal dimensions.*—Slightly broader (8.4 mm) than long (6.9 mm).

*Stamen collar.*—Color at opening of flower white 155D.

*Stamen collar 10–14 days after opening of flower.*—Color white 155D with red-purple 58A tinge.

*Gynoecium.*—1 pistil, stigma bearded, color yellow-orange 14D with style white 155D, with patches towards tip of red-purple 58A; length 7 mm.

*Androcoecium.*—About 10 fertile stamens with 10 infertile staminoids arranged alternatively on a collar adnate to junction of petals and calyx; filament length 1.5 mm, color white 155D aging to white 155D with tinges of red-purple 68B; staminode length 1 mm, color white 155D aging with tinges of red-purple 68B; anthers length about 0.6 mm, color greyed-orange 166B; pollen is sterile.

*Disease resistance.*—Moderate.

We claim:

1. A new and distinct waxflower plant substantially as shown and described herein.

* * * * *